US008810794B2

(12) United States Patent
Breviere et al.

(10) Patent No.: US 8,810,794 B2
(45) Date of Patent: Aug. 19, 2014

(54) DEVICE FOR QUANTIFYING THE RELATIVE CONTENTS OF TWO ISOTOPES OF AT LEAST ONE SPECIFIC GASEOUS CONSTITUENT CONTAINED IN A GASEOUS SAMPLE FROM A FLUID, RELATED ASSEMBLY AND PROCESS

(75) Inventors: Jérôme Breviere, Taverny (FR); Douglas Baer, Menlo Park, CA (US); Michael John Whiticar, Victoria (CA)

(73) Assignee: Geoservices Equipements, Cedex (FR)

( * ) Notice: Subject to any disclaimer, the term of this patent is extended or adjusted under 35 U.S.C. 154(b) by 403 days.

(21) Appl. No.: 12/309,964

(22) PCT Filed: Aug. 10, 2007

(86) PCT No.: PCT/IB2007/002317
§ 371 (c)(1),
(2), (4) Date: Sep. 28, 2009

(87) PCT Pub. No.: WO2008/017949
PCT Pub. Date: Feb. 14, 2008

(65) Prior Publication Data
US 2010/0031732 A1    Feb. 11, 2010

(30) Foreign Application Priority Data
Aug. 11, 2006 (EP) .................................. 06291304

(51) Int. Cl.
*G01N 21/00* (2006.01)
(52) U.S. Cl.
USPC ......................................... 356/432; 356/435
(58) Field of Classification Search
USPC ................................................ 356/432, 435
See application file for complete search history.

(56) References Cited

U.S. PATENT DOCUMENTS 3,137,758 A * 6/1964 Mason et al. ................ 356/320
3,649,201 A    3/1972 Scalan
(Continued)

FOREIGN PATENT DOCUMENTS

EP    1 508 794    2/2005

OTHER PUBLICATIONS

International Search Report issued Nov. 20, 2007 in the International (PCT) Application of which the present application is the U.S. National Stage.

(Continued)

*Primary Examiner* — Tarifur Chowdhury
*Assistant Examiner* — Isiaka Akanbi
(74) *Attorney, Agent, or Firm* — Wenderoth, Lind & Ponack, L.L.P.

(57) ABSTRACT

A device includes a device for forming a gaseous flow from the sample and a device for separation of each specific gaseous constituent. The device also includes a device for quantifying the relative contents of the two isotopes to be analyzed which comprise an optical measurement cell. The cell includes two mirrors which delimit a measurement cavity. The device includes a device for introducing an incident optical signal into the measurement cavity, a device for generating a plurality of reflections of the signal in separate points on each mirror during its travel in the cavity, a device for measuring a transmitted optical signal resulting from an interaction between the optical signal and each isotope in the measurement cavity, and a device for calculating the relative contents on the basis of these signals.

21 Claims, 4 Drawing Sheets

(56) References Cited

U.S. PATENT DOCUMENTS

| | | | |
|---|---|---|---|
| 3,847,549 A | 11/1974 | Schorno | |
| 4,082,633 A * | 4/1978 | Eerkens | 204/157.22 |
| 4,440,013 A | 4/1984 | Adams | |
| 4,517,461 A | 5/1985 | Crandall | |
| 4,587,835 A | 5/1986 | Adams | |
| 4,833,915 A | 5/1989 | Radd et al. | |
| 5,012,052 A | 4/1991 | Hayes | |
| 5,015,348 A * | 5/1991 | Eerkens | 204/157.2 |
| 5,090,256 A | 2/1992 | Issenmann | |
| 5,110,430 A * | 5/1992 | Eerkens | 204/157.2 |
| 5,246,868 A | 9/1993 | Busch et al. | |
| 5,388,456 A | 2/1995 | Kettel | |
| 5,394,236 A | 2/1995 | Murnick | |
| 5,783,445 A | 7/1998 | Murnick | |
| 5,783,741 A | 7/1998 | Ellis et al. | |
| 5,818,580 A | 10/1998 | Murnick | |
| 5,828,687 A | 10/1998 | Colgan | |
| 5,864,398 A | 1/1999 | Murnick | |
| 6,443,001 B1 | 9/2002 | Duriez et al. | |
| 6,611,333 B1 * | 8/2003 | Uehara et al. | 356/432 |
| 6,888,127 B2 | 5/2005 | Jones et al. | |
| 2004/0014223 A1 | 1/2004 | Audibert et al. | |
| 2005/0099618 A1 | 5/2005 | DiFoggio et al. | |
| 2007/0178011 A1 * | 8/2007 | Elrod et al. | 422/78 |

OTHER PUBLICATIONS

Written Opinion of the International Searching Authority issued Nov. 20, 2007 in the International (PCT) Application of which the present application is the U.S. National Stage.

Uehara et al., "Isotope analysis of environmental substances by a new laser-spectroscopic method utilizing different pathlengths", *Sensors and Actuators*, B 74, pp. 173-178, 2001.

* cited by examiner

DEVICE FOR QUANTIFYING THE RELATIVE CONTENTS OF TWO ISOTOPES OF AT LEAST ONE SPECIFIC GASEOUS CONSTITUENT CONTAINED IN A GASEOUS SAMPLE FROM A FLUID, RELATED ASSEMBLY AND PROCESS

BACKGROUND OF THE INVENTION

I. Field of Invention

The present invention relates to a quantification device for quantifying the relative contents of two isotopes of at least one specific gaseous constituent contained in a gaseous sample from a fluid, of the type comprising a means for forming a gaseous flow from the sample, comprising means for separation by means of selective retention of the or each specific gaseous constituent, a means for quantifying the relative contents of the two isotopes to be analysed of the or each specific constituent.

This device is used in particular to analyse the gases extracted from a petroleum fluid produced in an oil well or to determine extracted gas composition from a drilling fluid.

II. Description of the Related Art

In the last case, when an oil or other outflow well is drilled (in particular gas, vapour, water), it is known to carry out an analysis of the gaseous compounds contained in the drilling mud originating from the well. This analysis allows the geological sequence of the formations passed through during the drilling operation to be reconstructed and is used to determine the possible applications of the fluid deposits encountered.

This analysis, which is carried out in a continuous manner, comprises two main phases. The first phase consists in extracting the gases carried by the mud (for example, hydrocarbon compounds, carbon dioxide, hydrogen sulphide). The second phase consists in qualifying and quantifying the extracted gases.

In order to extract the gases from the mud, a degassing means with mechanical agitation of the type described in FR 2 799 790 is often used. The gases extracted from the mud, mixed with a carrier gas which is introduced into the degassing means, are conveyed by means of suction through a gas extraction pipe to an analysis device which allows the extracted gases to be quantified.

The analysis device comprises a gas-phase chromatograph (GPC) which allows the various gases collected in the degassing means to be separated in order to be able to quantify them.

In some cases, however, it is necessary to carry out a more precise analysis of the gaseous content of the extracted gases, using a device for measuring the relationship between the contents of carbon isotopes $^{13}C$ and $^{12}C$ in the gaseous hydrocarbon compounds extracted from the mud.

A device of this type comprises, in conjunction with the gas-phase chromatography, a combustion oven and an isotope ratio mass spectrometer (IRMS) which is intended to analyse the outflow from the combustion oven.

A device of this type is unsatisfactory, in particular when the analysis must be carried out on a drilling site or on a production site. The IRMS must be kept in a vibration free environment under pressure and temperature conditions which are substantially constant in order to obtain precise and repetitive measurements. Consequently, it is necessary to carry out an "off-line" analysis of the samples in a climate-controlled laboratory. If it is desirable to carry out the analysis "on-line", however, it is necessary to bring a large, fragile and complex climate control and an IRMS control assembly close to the well in an environment which can be hostile and inaccessible.

SUMMARY OF THE INVENTION

An objective of the invention is therefore to provide a device for isotopic measurements of at least one gaseous constituent from a fluid, which device can readily be arranged in the vicinity of an oil well or a drilling site in order to obtain "on-line" measurements while maintaining an adequate level of measurement precision for the analysis.

To this end, the invention relates to a device of the above-mentioned type, characterised in that the quantification means or device comprises:
  an optical measurement cell which is connected to the separation means or device, the measurement cell comprising;
  at least two mirrors which delimit a measurement cavity; and
  a means or device for transporting the gaseous flow to the measurement cavity;
  a means or device for introducing a laser incident optical signal having a variable wavelength into the measurement cavity;
  a means or device for generating a plurality of reflections of the optical signal in at least two separate points on each mirror during its travel in the cavity;
  a means or device for measuring a transmitted optical signal resulting from an interaction between the optical signal and each isotope in the measurement cavity; and
  a means or device for calculating the relative contents on the basis of the transmitted optical signal.

The device according to the invention may comprise one or more of the following features, taken in isolation or according to all technically possible combinations:
  the quantification means comprises a means or device for emitting a optical signal, and a means or device or optically transmitting this signal to the introduction means, and the emission means comprises a means or device for adjusting the wavelength of the emitted signal, which means is able to scan a specific wavelength range for a predetermined period of time;
  the cell comprises a means or device for trapping the component to be analysed in the measurement cavity;
  at least a first mirror has a reflectivity of less than 100%, the measurement means being arranged at the rear of the first mirror outside of the measurement cavity;
  the mirrors are arranged opposite to each other along a cavity axis, the mirrors having reflective surfaces which are arranged coaxially along the cavity axis;
  the means for generating a plurality of reflections comprises a means or device for inclining the introduction means to incline the incident optical signal to be introduced into the measurement cavity relative to the cavity axis, at least two separate optical signal segments in the measurement cavity being created by the means for generating a plurality of reflections;
  the introduction means comprises a means or device for positioning the injection point of the incident optical signal into the measurement cavity with spacing from the cavity axis;
  the separation means comprises a gas-phase chromatograph; and
  it has no means or device for combustion of the gaseous flow.

The invention further relates to an assembly for analysing at least one gaseous constituent contained in a petroleum fluid, of the type comprising:
- a means or device for sampling the petroleum fluid;
- a means or device for extracting a gaseous sample from the fluid, which means is connected to the sampling means; and
- a device as defined above, the extraction means being connected to the formation means.

The invention also relates to a method for quantifying the relative contents of two isotopes of at least one specific gaseous constituent contained in a gaseous sample from a fluid, of the type comprising the following steps:
- the formation of a gaseous flow from the sample, comprising a separation phase by means of selective retention of the or each specific gaseous constituent;
- the quantification of the relative contents of the two isotopes to be analysed of the or each specific constituent;
- characterised in that the quantification step comprises:
- the introduction of the gaseous flow from the separation phase into an optical measurement cell, the measurement cell comprising at least two mirrors which delimit a measurement cavity;
- the transportation of the gaseous flow to the measurement cavity;
- the introduction of a laser incident optical signal having a variable wavelength into the measurement cavity;
- the generation of a plurality of reflections of the optical signal in at least two separate points on each mirror during its travel in the cavity;
- the measurement of a transmitted optical signal resulting from an interaction between the optical signal and each isotope in the measurement cavity; and
- the calculation of said relative contents on the basis of the transmitted optical signal.

The method according to the invention may comprise one or more of the following features, taken in isolation or according to all technically possible combinations:
- the quantification step includes the trapping of the component to be analysed in the measurement cavity;
- the quantification step comprises a phase for emitting a substantially monochromatic optical signal, and a phase for optically transmitting this signal in order to introduce it into the measurement cavity and the emission phase comprises the adjustment of the wavelength of the signal generated, and the scanning of a specific wavelength range for a predetermined period of time;
- at least a first mirror has a reflectivity of less than 100%, the measurement step being carried out at the rear of the first mirror outside of the measurement cavity;
- the mirrors are arranged opposite to each other along a cavity axis, the mirror having reflective surfaces which are arranged coaxially along the cavity axis, the reflections being created between the surfaces;
- the step for generating a plurality of reflections comprises the inclination of the incident optical signal to be introduced into the measurement cavity relative to the cavity axis in order to create at least two separate optical signal segments in the measurement cavity;
- the introduction step comprises the positioning of the injection point of the incident optical signal into the measurement cavity with spacing from the cavity axis; and
- there is no step for combustion of the gaseous flow.

BRIEF DESCRIPTION OF THE DRAWINGS

The invention will be better understood from a reading of the following description, given purely by way of example and with reference to the appended drawings, in which.

DETAILED DESCRIPTION OF THE INVENTION

A quantification device according to the invention is, for example, used in an analysis assembly 9 used for the on-line analysis of the gaseous content of drilling mud in an installation 11 for drilling an oil production well.

Figure 1:
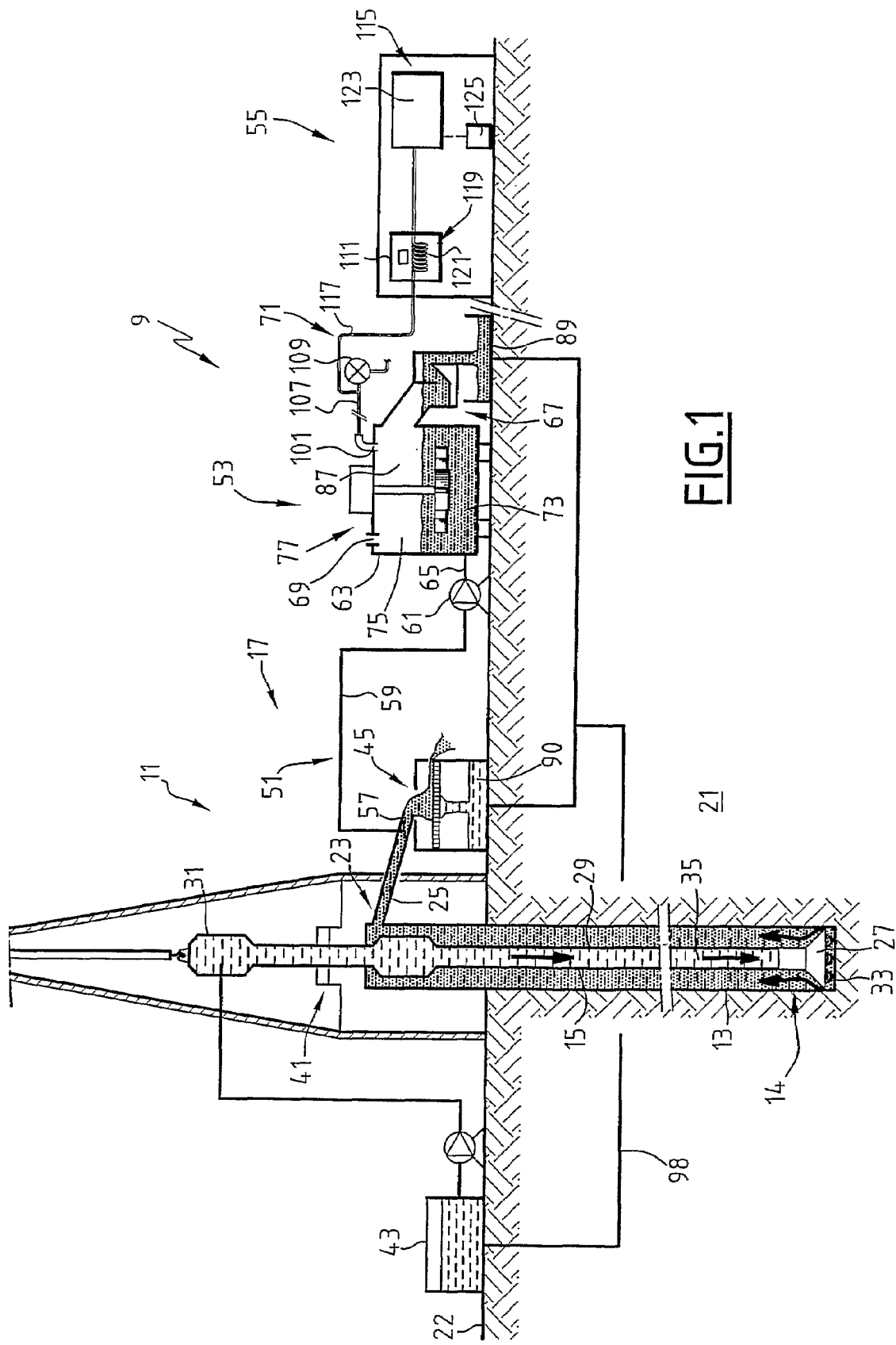
FIG. 1 is a schematic sectioned view of an analysis assembly according to the invention, arranged in an installation for drilling an oil well.

As illustrated in FIG. 1, this installation 11 comprises a drilling pipe 13 in a cavity 14 through which a rotating drilling tool 15 extends, and a surface installation 17.

The drilling pipe comprises, in the region of the surface 22, a well head 23 which is provided with a pipe 25 for discharging a drilling fluid, referred to as drilling mud.

The drilling tool 15 comprises a drilling head 27, a drilling assembly 29 and a liquid injection head 31.

The drilling head 27 comprises means 33 for drilling through the rocks of the sub-stratum 21. It is assembled in the lower portion of the drilling assembly 29 and is positioned at the bottom of the drilling pipe 13.

The assembly 29 comprises an assembly of hollow drilling tubes. These tubes delimit an internal space 35 which allows a liquid to be conveyed from the surface 22 to the drilling head 27. To this end, the liquid injection head 31 is screwed onto the upper portion of the assembly 29.

The surface installation 17 comprises means 41 for supporting and driving the drilling tool 15 in rotation, means 43 for injecting drilling liquid and a vibrating sieve 45.

The injection means 43 is hydraulically connected to the injection head 31 in order to introduce and circulate a liquid in the inner space 35 of the drilling assembly 29.

The vibrating sieve 45 collects the liquid charged with drilling residues which is discharged from the discharge pipe 25 and separates the liquid from the solid drilling residues.

Figure 2:
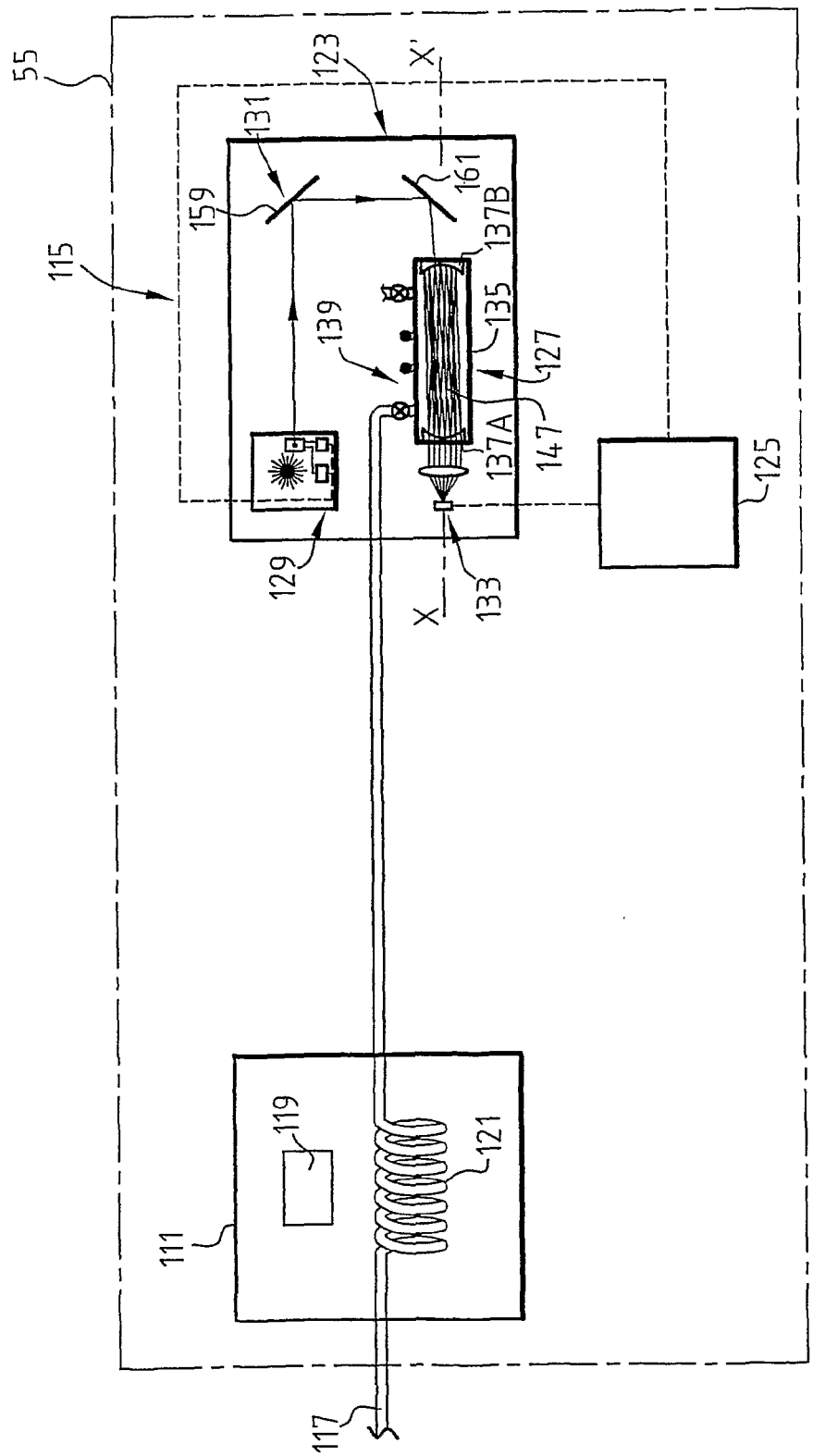
FIG. 2 is a detailed view of a first quantification device according to the invention in the analysis assembly of FIG. 1.

As illustrated in FIG. 2, the analysis assembly 9 comprises means 51 for sampling the mud, which means is tapped into the discharge pipe 25, a gas extraction device 53, and a device 55 for analysing and quantifying the extracted gases.

The sampling means 51 comprises a liquid sampling head 57 which is tapped into the discharge pipe 25, a connection tube 59 and a peristaltic pump 61 whose flow rate can be adjusted.

The extraction device 53 comprises a vessel 63, a pipe 65 for conveying the mud into the vessel 63, a pipe 67 for discharging the mud from the vessel 63, an inlet 69 for introducing a carrier gas into the vessel 63, and a pipe 71 for extracting the extracted gases from the vessel 63.

The vessel 63 is formed by a sealed receptacle whose inner volume is, for example, between 0.4 and 3 liters. This vessel 63 comprises a lower portion 73 in which the mud circulates and an upper portion 75 which has a gaseous cap. The vessel 63 is further provided with an agitator 77 which is immersed in the mud.

The mud supply pipe 65 extends between the outlet of the peristaltic pump 61 and an inlet opening which is arranged in the lower portion 73 of the vessel 63.

This supply pipe 65 may be provided with means for heating the mud (not illustrated) in order to bring the temperature of this mud to values between 25 and 120° C., preferably between 60 and 90° C.

The discharge pipe 67 extends between an overflow passage 87 which is arranged in the upper portion 75 of the vessel 63 and a retaining vessel 89 which is intended to receive the mud which is discharged from the device 53. It comprises a siphon in order to prevent gas from being introduced into the upper portion 75 of the vessel 63 via the discharge pipe 67. Gas is therefore introduced into the vessel 63 only via the carrier gas introduction inlet 69.

The mud which is collected in the retaining vessel 89 is recycled towards the injection means 43 via a mud recirculation pipe 98.

The gas extraction pipe 71 extends between an extraction opening 101, which is arranged in the upper portion 75 of the vessel 63, and the analysis device 55. It comprises a transport line 107 which is provided with volume flow control means and suction means 109.

The transport line 107 connects the vessel 63 which is arranged in the vicinity of the well head 23, in the explosive zone, to the analysis device 55 which is arranged with spacing from the well head 23 in a non-explosive zone, for example, in a pressurised cabin.

This transport line 107 can be produced on the basis of a polymer material, known to be inert versus hydrocarbons, such as PTFE or THV, and has, for example, a length of from 10 m to 500 m.

The suction means 109 comprise a vacuum pump which allows the gases extracted from the vessel 63 to be conveyed, by means of suction, to the analysis device 55.

As illustrated in FIG. 2, the analysis device 55 according to the invention comprises a stage 111 for forming a gaseous flow to be analysed, and a stage 115 for quantifying the content of the gaseous constituents to be analysed in the drilling mud, which stage is directly connected to an outlet of the formation stage. The analysis device is therefore deprived of combustion means inserted between the formation stage 111 and the quantification stage 115.

The formation stage 111 comprises a sampling pipe 117 which is tapped into the extraction pipe 71 in the vicinity of the pump 109, upstream of this pump, and a gas-phase chromatograph 119 which is provided with a column 121 for separation by means of selective retention of the gaseous constituents to be analysed.

The chromatograph 119 is, for example, a gas chromatograph as known by those of skilled in the art, with a gas injection system and a chromatographic separation column 121 to separate compounds to be analyzed before quantification in the quantification device 115.

The separation column 121 has a length which is between 2 m and 25 m in order to ensure a mean passage time for the gases of between 30 s and 600 s. It is connected to the sampling pipe 117 in order to take a gaseous sample from the extraction pipe 71 and form a gaseous flow at the outlet of the column 121, in which flow the sample constituents to be analysed are separated over time.

The quantification stage 115 comprises an optical measurement unit 123 which is connected directly to an outlet of column 121, and a control and calculation unit 125 which is connected electrically to the measurement unit 123.

Figure 3:
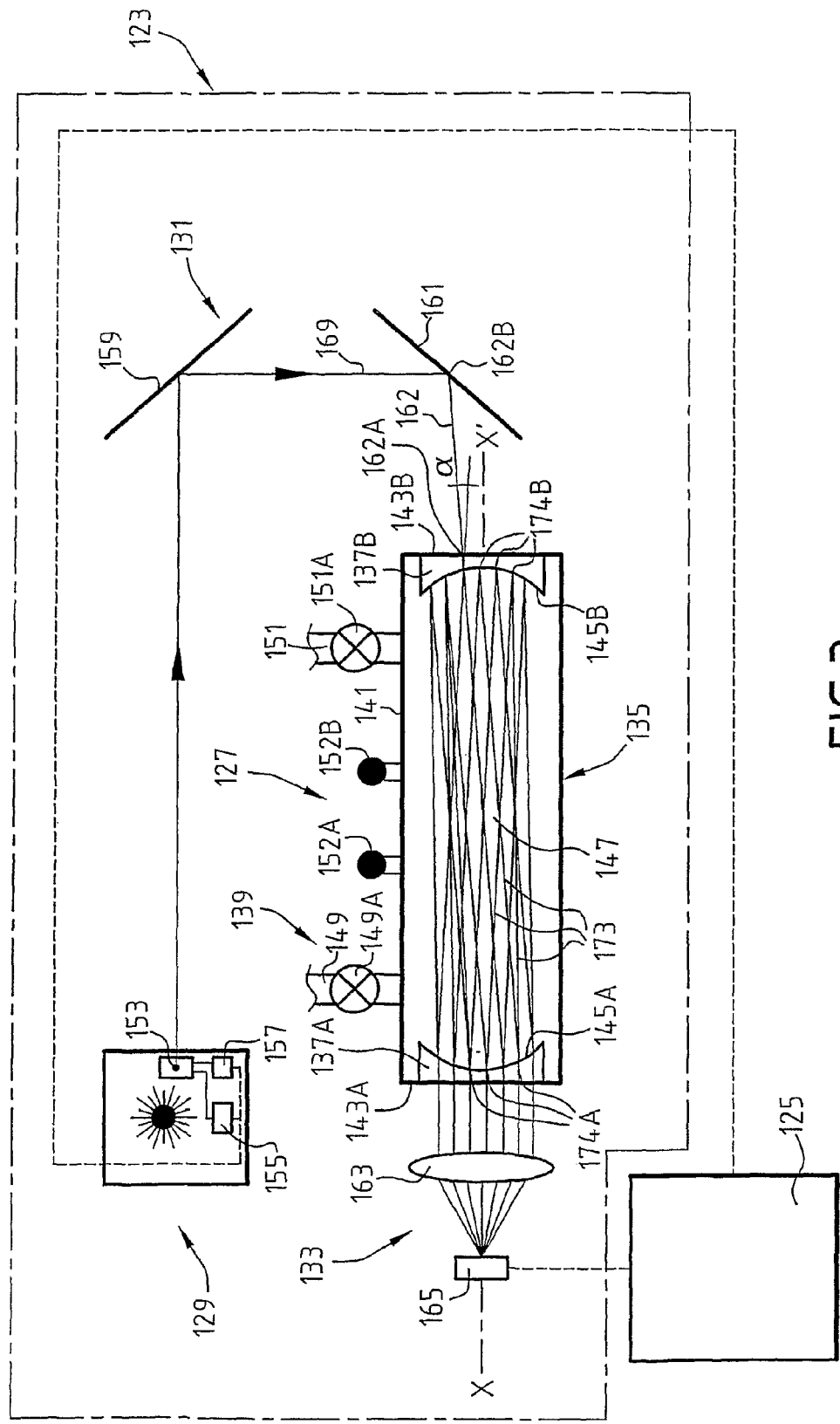
FIG. 3 is a partially sectioned schematic view of the optical measurement means of the device of FIG. 2 comprising in particular a laser and a sensor.

As illustrated in FIGS. 2 and 3, the optical measurement unit 123 comprises an optical measurement cell 127, a laser 129 for emitting an optical incident signal, a mechanism 131 for introducing the optical signal into the cell 127, and a sensor 133 for measuring an optical signal transmitted from the cell 127.

The cell 127 comprises a confinement chamber 135, two concave mirrors 137A, 137B which are fixed in the chamber 135 and means 139 for transporting the gaseous flow from the combustion oven into the chamber 135.

With reference to FIG. 3, the chamber 135 comprises a cylindrical wall 141 which extends substantially along a longitudinal centre axis X-X', and two planar end walls 143A, 143B which longitudinally close the cylindrical wall 141.

The end walls 143A, 143B are transparent with respect to wavelengths in the near infrared regions such as 1100 nm, 1600 nm or 2100 nm region.

Each mirror 137A, 137B is fixed in the chamber 135 to a corresponding end wall 143A, 143B. The mirrors 137A, 137B are fixed coaxially along the axis X-X'. Each mirror 137A, 137B has a substantially spherical, concave reflective surface 145A, 145B which is directed towards the inner side of the chamber 135.

The radius of curvature of the concave surfaces 145A, 145B is, for example, between 4 m and 8 m. The reflectivity of the mirrors 135A, 137B is greater than 50% and preferably greater than 99% for wavelengths in the near infrared regions as specified above.

The surfaces 145A, 145B extend opposite each other symmetrically relative to a vertical centre plane of the chamber 135. Together they delimit, in the chamber 135, an absorption measurement cavity 147 for the interaction between an optical signal and the constituents which are introduced into the cavity 147 by the transportation means 139. The distance which separates the surfaces 145A, 145B is generally between 50 cm and 90 cm.

The transportation means 139 comprises a pipe 149 for introducing the gaseous flow into the chamber and a discharge pipe 151. Each pipe 149, 151 is provided with a flow rate control valve 149A, 151A.

The introduction pipe 149 is connected to an outlet of the combustion oven 133. It opens into the chamber 135 through the wall 141, in the vicinity of the upstream mirror 137A.

The discharge pipe 151 also opens into the chamber 135 in the vicinity of the downstream mirror 137.

The chamber 135 is provided with respective temperature and pressure control means 152A, 152B.

The laser 129 comprises a cavity 153 for emitting a light ray which forms a substantially monochromatic optical signal, means 155 for adjusting the mean wavelength of the signal, and means 157 for controlling the intensity of the signal.

A substantially monochromatic signal is understood to be a signal which has a width at mid-range of, for example, between 0.05 nm and 1 nm.

The means 157 for controlling the intensity can generate a signal having substantially constant intensity for a variable period of time.

The transmission and introduction mechanism 131 comprises a deflection mirror 159 which is arranged opposite the emission cavity 153 and a mirror 161 for adjusting the angle of injection into the measurement cavity 147, which mirror is arranged opposite the downstream mirror 143B at the outer side of the chamber 135, and is arranged opposite the deflection mirror 159.

The adjustment mirror 161 is provided with means for adjusting the injection angle α formed by the longitudinal axis X-X' and the axis of the segment 162 of the optical incident signal introduced into the cavity 147, taken between the reflection point 162B thereof on the mirror 161 and the introduction point 162A thereof in the chamber 135.

The mirror 161 is further provided with means for transverse displacement relative to the axis X-X' in order to position the introduction point 162A with spacing from the axis X-X'.

The sensor 133 for measuring the transmitted optical signal comprises a focussing lens 163 which extends perpendicularly relative to the axis X-X' at the rear of the upstream mirror 137A at the outer side of the chamber 135, and an intensity detector 165 which is arranged at the focal point of the lens 163 located on the axis X-X' opposite the chamber 135 relative to the lens 163. The detector 165 is electrically connected to the control and calculation unit 125.

A first method for quantifying a constituent which is contained in a gaseous sample taken from a drilling mud and which is carried out on-line when a well is drilled will now be described with reference to FIG. 1.

In order to carry out the drilling operation, the drilling tool 15 is driven in rotation by the surface installation 41. A drilling liquid is introduced into the inner space 35 of the drilling assembly 29 by the injection means 43. This liquid moves downwards as far as the drilling head 27 and passes into the drilling pipe 13 through the drilling head 27. This liquid cools and lubricates the drilling means 33. Then the liquid collects the solid debris resulting from the drilling operation and moves upwards again through the annular space which is defined between the drilling assembly 29 and the walls of the drilling pipe 13, then is discharged via the discharge pipe 25.

The peristaltic pump 61 is then activated in order to remove, in a continuous manner, a specific fraction of the drilling mud which is circulating in the pipe 25.

This fraction of mud is conveyed as far as the chamber 63 via the supply pipe 65.

The agitator 77 is driven in rotation in the lower portion 73 of the chamber 63 in order to bring about the extraction of the gases contained in the mud and the mixture of the extracted gases with the carrier gas drawn through the injection inlet 69.

The gaseous mixture is extracted via the extraction pipe 71, under the action of the suction produced by the vacuum pump 109. This mixture is then conveyed as far as the analysis device 55.

The gaseous mixture containing a plurality of constituents to be analysed is then injected into the chromatograph 119 through the sampling pipe 117. A gaseous flow, in which the various constituents to be analysed in the gaseous mixture are separated over time, is then obtained at the outlet of the column 121. This gaseous flow successively comprises, for example, $C_1$ hydrocarbons, then $C_2$ hydrocarbons then $CO_2$, then other heavier compounds. The gaseous flow then enters the optical measurement unit 123.

In case the constituent is a hydrocarbon, the isotopes to be analysed are those of carbon, i.e. $^{12}C$ carbon and $^{13}C$ carbon. If the constituent is water, the isotopes to be analysed are those of oxygen.

In the unit 123, the various constituents are successively introduced into the chamber 135 and flow in the optical cavity 147 from the introduction pipe 149 to the discharge pipe 151.

Figure 4:
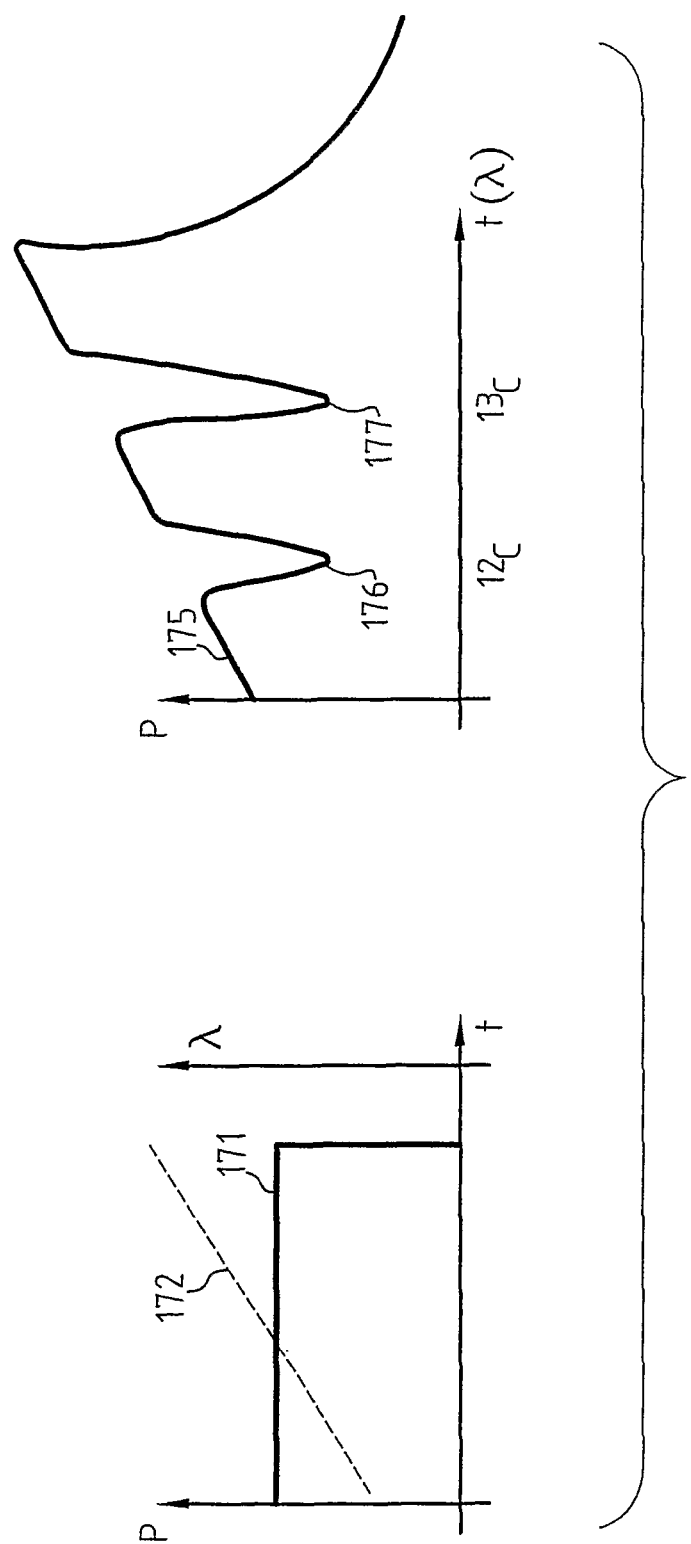
FIG. 4 is a view illustrating the emission line of the laser of FIG. 3 as a function of time, and the reception line measured by the sensor of FIG. 3 as a function of time when a method according to the invention is used.

In the method according to the invention, immediately after the first component to be analysed has entered in the cavity 147, the cavity 147 is isolated from the gaseous flow with valves 149A and 151A to perform quantification. Then the means 155 for adjusting the wavelength are controlled to scan a wavelength range in the near infrared regions such as 1100 nm, 1600 nm or 2100 nm region (line 172 in FIG. 4) for a predetermined period of time.

A scanning operation of this type is repeated for each passage of the various constituents which are to be analysed and which circulate successively in the measurement cavity 147 after opening of valves 149A and 151A.

The laser incident signal 169 is conveyed as far as the optical cavity 147 by means of reflection on the deflection mirror 159 and the adjustment mirror 161 then by transmission through the wall 143B and the mirror 137B.

The laser signal is introduced into the cavity 147 at a point 162A which is located with spacing from the axis X-X'. The injection angle α is set different from zero.

The optical signal then travels along an optical path back and forth in the measurement cavity 147, formed by successive separate segments 173 which are delimited by a plurality of discrete reflection points 174B on each concave surface 145A, 145B. This plurality of reflections is generated by the control of the inclination of the mirror 161.

The optical signal therefore covers an optical path which comprises at least 100 segments in the measurement cavity 147, and preferably at least 1000 segments.

Given the weak interactions between the various segments 173 of the optical signal formed between the successive reflection points 174A, 174B of the signal on the mirrors 137A, 137B, the measurement cavity 147 has no selectivity with respect to the transmission wavelength and it is not necessary to modify the length of the cavity 147 in order to adapt to the wavelength. The optical measurement unit 123 therefore has no electronic components which are costly and difficult to use on an oil site.

The interaction of the various segments 173 and the various isotopes of the constituent contained in the measurement cavity 147 generates an optical signal which carries an item of information characteristic of the content of these isotopes in the measurement cavity 147.

The optical signal interacts with the molecular constituents of the measurement cell by means of vibrational excitation. The molecules absorb a portion of the optical signal resulting in a loss of optical intensity. This occurs in each segment 173 which is transmitted through the upstream mirror 137A and which is not reflected on the surface 145A.

The transmitted optical signal is focussed through the lens 163 and detected by the sensor 165 in order to obtain the intensity 175 as a function of time illustrated in FIG. 4(b).

Furthermore, the range of the wavelength of the optical signal is adjusted in order to scan a range in which two characteristic absorptions of two respective isotopes of the same element are produced, for example, carbon $^{12}C$ and carbon $^{13}C$, the intensity 175 of the transmitted optical signal as a function of the wavelength shows two respective characteristic absorption regions 176 and 177 of these two isotopes. The relationship of the contents of two isotopes of the same constituent, for example, the $C_1$ hydrocarbons, in the drilling mud is then calculated on the basis of the relationship between the depths of the regions 176 and 177, with reference to a baseline taken out of the absorption regions.

Additionally, the decay time of the intensity 175 of the transmitted signal can be used to quantify the absolute quantity of each constituent.

The method is then repeated during the successive passage of each constituent to be analysed in the cavity 147.

Owing to the invention which has been described above, it is possible to provide a device 55 for isotopic measurements in a sample from a petroleum fluid, which can be readily fitted in the vicinity of a drilling installation or a well for the exploitation of fluids.

The combination of means 111 for forming a gaseous flow comprising a column 121 for separation by means of selective retention, with a unit 115 for optical measurement of the content of the isotopes of the constituents separated by the column 121 allows "on-line" analysis of the gaseous compounds extracted from a drilling fluid or a fluid coming from a well, whilst retaining a significant level of selectivity for carrying out valuable isotopic measurements.

Furthermore, the use of an optical measurement unit 115, comprising a reflective absorption cavity 147 in which the incidence of the optical signal injected into the cavity 147 is not zero, considerably simplifies the instruments required, which allows the quantification device 55 to be readily displaced and positioned in the vicinity of a drilling installation or an oil well.

As shown in FIGS. 2 and 3, a single laser 129 having a unique cavity 153 is used in the optical measurement unit 123.

The range of wavelengths generated by the laser 129 when the scanning of the constituents in the cavity 147 is performed is wide enough to obtain two distinguishing absorptions regions corresponding to the two distinct isotopes, e.g. for carbon $^{12}C$ and carbon $^{13}C$, without the need for using two different laser sources, Moreover, the laser incident signal 169 produced in the cavity 153 is fully conveyed towards the cavity 147 without significant absorption on its path towards the cavity 147. The signal 169 is not split or passed through a reference cell containing a reference sample.

The device 55 is deprived of such a reference cell, which is not necessary for obtaining the isotopic ratios.

The invention claimed is:

1. A device for quantifying the relative contents of two isotopes of at least one specific gaseous constituent contained in a gaseous sample from a fluid, said device comprising:
a forming device configured to form a gaseous flow from the sample, said forming device comprising a separation device having a column configured to separate the gaseous sample by selective retention of the or each specific gaseous constituent to obtain a gas flow in which the or each specific gaseous constituent is separated over time at an outlet of said column;
a quantifying device configured to quantify relative contents of the two isotopes of the or each specific gaseous constituent;
wherein the quantifying device comprises:
an optical measurement cell connected to said separation device, said optical measurement cell comprising at least two mirrors which delimit a measurement cavity, and a transporting device configured to transport the gaseous flow to the measurement cavity;
an introducing device configured to introduce a laser incident optical signal having a variable wavelength into the measurement cavity;
a generating device configured to generate a plurality of reflections of the laser incident optical signal in at least two separate points on each of said at least two mirrors during travel of the laser incident optical signal in the cavity;
a measuring device configured to measure a transmitted optical signal resulting from an interaction between the laser incident optical signal and each isotope of the two isotopes in the measurement cavity;
a calculating device configured to calculate the relative contents on the basis of the transmitted optical signal; and
an optical measurement unit comprising said optical measurement cell, said optical measurement unit being directly connected to the outlet of said column, such that the gaseous flow directly enters the optical measurement unit free from chemical modification of the gaseous flow.

2. A device according to claim 1, wherein said quantifying device comprises an emitting device configured to emit an optical signal, and a transmitting device configured to optically transmit the optical signal emitted from said emitting device to said introducing device, and said emitting device comprises an adjusting device configured to adjust the wavelength of the optical signal emitted from said emitting device, said adjusting device capable of scanning a specific wavelength range for a predetermined period of time.

3. A device according to claim 1, wherein said cell comprises a trapping device configured to trap the isotopes to be analysed in the measurement cavity.

4. A device according to claim 1, wherein at least a first mirror of said at least two mirrors has a reflectivity of less than 100%, and said measuring device is arranged at a rear of said first mirror outside of the measurement cavity.

5. A device according to claim 1 wherein said at least two mirrors are arranged opposite to each other along a cavity axis, said at least two mirrors having reflective surfaces which are arranged coaxially along the cavity axis.

6. A device according to claim 5, wherein said generating device comprises an inclining device configured to incline said introducing device so as to incline the incident optical signal to be introduced into the measurement cavity relative to the cavity axis, at least two separate optical signal segments in the measurement cavity being created by said generating device.

7. A device according to claim 5, wherein said introducing device comprises a positioning device configured to position an injection point of the incident optical signal into the measurement cavity with spacing from the cavity axis.

8. A device according to claim 1, wherein said separating device comprises a gas-phase chromatograph.

9. A device according to claim 1, further comprising no device to combust the gaseous flow.

10. An assembly for analysing at least one gaseous constituent contained in a petroleum fluid, said assembly comprising:
a sampling device configured to sample the petroleum fluid;
an extracting device configured to extract a gaseous sample from the fluid, said extracting device being connected to said sampling device; and
a device according to claim 1, wherein said extracting device is connected to said forming device.

11. A device according to claim 1, further comprising a single laser having a unique cavity, said single laser configured to be used in the optical measurement unit for measuring both isotopes, such that the range of wavelengths generated by said laser, when the scanning of the constituents in the cavity is performed, is wide enough to obtain two distinguishing absorption regions corresponding to the two distinct isotopes without using two different laser sources.

12. A device according to claim 1, wherein said separation device is disposed upstream of the cavity.

13. A method for quantifying the relative contents of two isotopes of at least one specific gaseous constituent contained in a gaseous sample from a fluid, said method comprising:
forming a gaseous flow from the sample, said forming comprising a separation phase by selective retention of the or each specific gaseous constituent;
quantifying the relative contents of the two isotopes of the or each specific constituent;
wherein said quantifying comprises:

introducing the gaseous flow from the separation phase directly into an optical measurement cell free from chemical modification of the gaseous flow, the measurement cell comprising at least two mirrors which delimit a measurement cavity;

transporting the gaseous flow to the measurement cavity;

introducing a laser incident optical signal having a variable wavelength into the measurement cavity;

generating a plurality of reflections of the laser incident optical signal in at least two separate points on each mirror during travel of the optical signal in the cavity;

measuring a transmitted optical signal resulting from an interaction between the laser incident optical signal and each isotope of the two isotopes in the measurement cavity; and calculating the relative contents on the basis of the transmitted optical signal.

14. A method according to claim 13, wherein said quantifying includes trapping the isotopes in the measurement cavity.

15. A method according to claim 13, wherein said quantifying comprises a phase emitting a substantially monochromatic optical signal, and a phase optically transmitting the substantially monochromatic optical signal to introduce the substantially monochromatic optical signal into the measurement cavity and said emitting phase comprises adjusting the wavelength of the signal generated, and scanning of a specific wavelength range for a predetermined period of time.

16. A method according to claim 13, wherein at least a first mirror of the at least two mirrors has a reflectivity of less than 100%, said measuring being carried out at the rear of the first mirror outside of the measurement cavity.

17. A method according to claim 13, wherein the at least two mirrors are arranged opposite to each other along a cavity axis, and have reflective surfaces which are arranged coaxially along the cavity axis, the reflections being created between the surfaces.

18. A method according to claim 17, wherein said generating a plurality of reflections comprises inclining the incident optical signal introduced into the measurement cavity relative to the cavity axis to create at least two separate optical signal segments in the measurement cavity.

19. A method according to claim 17, wherein said introducing comprises positioning an injection point of the incident optical signal into the measurement cavity with spacing from the cavity axis.

20. A method according to claim 17, further comprising no combusting of the gaseous flow.

21. A method for continuously quantifying the relative contents of two isotopes of at least one specific gaseous constituent contained in a gaseous sample from a fluid, said method comprising:

forming a gaseous flow from the sample, said forming comprising a separation phase by selective retention of the or each specific gaseous constituent;

quantifying the relative contents of the two isotopes of the or each specific constituent;

wherein said quantifying comprises:

introducing the gaseous flow from the separation phase directly into an optical measurement cell free from chemical modification of the gaseous flow, the measurement cell comprising at least two mirrors which delimit a measurement cavity;

transporting the gaseous flow to the measurement cavity;

introducing a laser incident optical signal having a variable wavelength into the measurement cavity;

generating a plurality of reflections of the laser incident optical signal in at least two separate points on each mirror during travel of the optical signal in the cavity;

measuring a transmitted optical signal resulting from an interaction between the laser incident optical signal and each isotope of the two isotopes in the measurement cavity; and calculating the relative contents on the basis of the transmitted optical signal.

* * * * *